United States Patent [19]

Ishizaka

[11] Patent Number: 5,723,582
[45] Date of Patent: Mar. 3, 1998

[54] ANTIGEN-SPECIFIC HUMAN GLYCOSYLATION INHIBITING FACTOR

[75] Inventor: Kimishige Ishizaka, La Jolla, Calif.

[73] Assignee: La Jolla Institute for Allergy and Immunology, La Jolla, Calif.

[21] Appl. No.: 458,221

[22] Filed: Jun. 2, 1995

Related U.S. Application Data

[60] Division of Ser. No. 142,333, filed as PCT/US92/04614, Jun. 3, 1992, Pat. No. 5,565,338, which is a continuation-in-part of Ser. No. 709,375, Jun. 3, 1991, abandoned, which is a continuation-in-part of Ser. No. 533,889, Jun. 4, 1990, abandoned.

[51] Int. Cl.$^6$ .................. C07K 14/47; C07K 14/52; C07K 16/42; A61K 39/00
[52] U.S. Cl. .................. 530/351; 530/350; 530/388.23; 530/387.2; 424/85.1; 424/131.1
[58] Field of Search .................. 435/69.1, 70.1, 435/183, 240.1; 514/8, 2, 12; 530/350, 351, 387.2, 388.23; 424/184.1, 131.1, 85.1

[56] References Cited

U.S. PATENT DOCUMENTS

| | | | |
|---|---|---|---|
| 4,545,986 | 10/1985 | Malley | 424/85 |
| 4,749,685 | 6/1988 | Martens et al. | 514/12 |
| 4,758,511 | 7/1988 | Martens et al. | 435/68 |
| 4,866,037 | 9/1989 | Delespesse | 514/8 |
| 4,898,730 | 2/1990 | Levy et al. | 424/88 |

OTHER PUBLICATIONS

Iwata et al., "Relationship Between T-Cell Receptors and Antigen-Binding Factors", *Journal of Immunology*, vol. 143, No. 12, Dec. 15, 1989, pp. 3909–3916.

Thomas et al., "Glycosylation–Inhibiting Factor From Human T Cell Hybridomas Constructed from Peripheral Blood Lymphocytes of a Bee Venom–Sensitive Allergic Patient", *Journal of Immunology*, vol. 148, No. 3, Feb. 1, 1992, pp. 729–737.

Carini et al. "A method to generate antigen–specific suppressor T cells . . . " *J. Immunol. Meth.* 127(2): 221–233 (Mar. 1990).

Thomas et al. "Construction of human T cell hybridomas . . . " *FASEB J.* 4(7):A1937, Abstract #1418 (Apr. 1990).

Steele et al. "A monoclonal antibody raised to lipomodulin . . . " *J. Immunol* 142(7): 2213–2220 (Apr. 1989).

Jardieu et al pp. 595–604 in *Immune Regulation by Characterized Polypeptides*, (Alan R. Liss, Inc. 1987).

Akasaki et al. "Immunosuppressive Effects of Glycosylation Inhibiting Factor on the IgE and IgG Antibody Response", *J. Immunol.* 136(9):3172–3179 (May 1986).

Iwada et al "Construction of Antigen–Specific Suppressor T Cell Hybridomas . . . " *J. Immunol.* 141(10): 3270–3277 (Nov. 1988).

Jardieu et al "Carrier–specific Suppression of Antibody Responses . . . " *J. Immunol.* 138(5): 1494–1501 (Mar. 1987).

Ohno et al "Effects of PLA$_2$ inhibitors on mouse T lymphocytes . . . " *Int. Immunol.* 1(4): 425, abstract. (1989).

Takeuchi et al, "Development of an Antigen–Specific CD8 Suppressor–Effector Clone in Man", *J. Immunol.* 141(9): 3010–3015.

*Primary Examiner*—Stephen Walsh
*Assistant Examiner*—Claire M. Kaufman
*Attorney, Agent, or Firm*—Fish & Richardson, P.C.

[57] ABSTRACT

The present invention provides antigen-specific human glycosylation inhibiting factor (GIF). Hybridoma cell lines ATCC HB 10473 and 11052 are provided as exemplary cell lines which produce human antigen-specific human GIF, directed toward honey bee venom and cedar pollen, respectively.

14 Claims, No Drawings

ANTIGEN-SPECIFIC HUMAN GLYCOSYLATION INHIBITING FACTOR

This application is a divisional application of Ser. No. 08/142,333, filed Jan. 27, 1993, now U.S. Pat. No. 5,565,338, which is a 371 of PCT/US93/04614, filed Jun. 3, 1992, and a continuation-in-part of Ser. No. 07/709,375, filed Jun. 3, 1991, now abandoned, which is a continuation-in-part of Ser. No. 07/533,889, filed Jun. 4, 1990, now abandoned.

This invention was made with Government support under grant numbers AI11202, AI14784, and AI32834 awarded by the National Institutes of Health. The Government has certain rights in the invention.

FIELD OF THE INVENTION

The invention relates to human glycosylation inhibiting factor (GIF) specific for an antigen and which can be used to suppress the human immune response to the antigen.

DESCRIPTION OF THE BACKGROUND ART

Although the immune response is often seen as beneficial, in certain circumstances the immune response to an antigen can actually be harmful to the animal in which the immune response occurs. An example where the immune response creates a condition wherein the best is subject to serious pathologic sequelae is in such autoimmune diseases as lupus erythematosus. In lupus erythematesus, antibodies are often present which react with determinants in the thyroid, erythrocytes, DNA, and platelets of the host.

Another example of where the suppression from immune response would be described is in the treatment of allergies. It has been established that IgE antibodies against allergens cause hay fever, and are involved in the other allergic diseases such as extrinsic asthma. The crucial role of IgE antibodies in the allergic diseases raised the possibility that the regulation and suppression of the IgE antibody formation against allergens would be one of the fundamental treatments for allergic diseases. For example, in the serum of hay fever patients sensitive to ragweed antigens, IgE antibodies against the allergens are always detected. The IgE antibody liter goes up after the pollen season, and then declines only slightly during the rest of the year. Since the half life of IgE in the serum is only 2 to 3 days, the persistence of the IgE antibody titer indicates that the antibodies are being synthesized continuously by the lymphoid cells of the patients in spite of the lack of allergen exposure.

Over the past 20 years, several different attempts were made to control the IgE antibody response in experimental animals. One of the approaches was to improve classical immunotherapy or desensitization treatment, in which allergic patients receive repeated injections of a minute dose of allergen. It was shown that the desensitization treatment can improve clinical symptoms in some patients. However, the IgE antibody titer in the serum of hay fever patients did not decline after the treatment. The major immunological effects of the treatment is an enhancement of the IgG antibody formation, and the suppression of an increase in the IgE antibody titer after the pollen season.

A limitation in the desensitization, or immunosuppression treatment is that patients cannot tolerate a large dose of allergen because of side effects. In order to overcome this difficulty, attempts were made to use a chemically modified allergen, such as urea-denatured antigen or polyethylene glycol (PEG)-conjugates of the antigen for the treatment. Since the modified antigens do not bind to antibodies against the native antigen relatively large doses of the modified antigen can be injected without causing allergic symptoms. However, the modified antigen can stimulate antigen-specific T-cells. Evidence was obtained that intravenous injections of the modified antigen into mice resulted in the generation of antigen-specific suppressor T-cells which suppressed the primary IgE antibody response to the native antigen. However, the treatment had minimal effects on the on-going IgE antibody formation, if the treatment were initiated after the antibody titer reached maximum (Takatsu and Ishizaka, *J. Immunol.,* 117:1211, 1976). In agreement with the observations in the mouse, clinical trials of polyethylene-glycol-conjugated allergen in hay fever patients showed that the treatment failed to diminish the IgE antibody titer. Failure of the repeated injections of the modified antigen to suppress the on-going IgE antibody formation is probably due to the presence of a relatively large population of antigen-specific helper T-cells in the allergic patients. Since the modified antigen not only induces the generation of antigen-specific suppressor T-cells, but also expands the population of helper T-cells, this latter effect of the treatment might have overcome the effect of suppressor T-cells. This interpretation is supported by the fact that transfer of antigen-specific suppressor T-cells into immunized mice resulted in the suppression of the on-going IgE antibody formation (Takatsu and Ishizaka, *J. Immunol.,* 117: 1211, 1976). The results collectively suggested that the persistent IgE antibody formation in hay fever patients could be suppressed, if it were possible to generate the antigen-specific suppressor T-cells without expanding the helper T-cell populations.

Since 1980, the inventors have investigated various ways in which IgE synthesis is selectively regulated in an immunoglobulin isotype-specific manner. As a result of this research, two types of T-cell factors have been found which have affinity for IgE and selectively regulate IgE synthesis. One of the IgE-binding factors (IgE-BF) selectively enhances the IgE response, while the other type of IgE-BF selectively suppresses the response. The major difference between the IgE-potentiating factors and IgE-suppressive factors appears to be carbohydrate moieties in the molecules. The IgE-potentiating factors bind to lentil lectin and concanavalin A, while IgE-suppressive factors fail to bind to these lectins (Yodoi, et al., *J. Immunol.,* 128: 289, 1982). Analysis of the cellular mechanism for the selective formation of either IgE-potentiating factors or IgE-suppressive factors, as well as gene cloning of the factors, indicated that the IgE-potentiating factor and IgE-suppressive factor share a common structural gene and that the nature of the carbohydrate moieties and biologic activities of the factors are established during the post-translational glycosylation process (Martens, et al, *Proc. Nat'l Acad. Sci., U.S.A.,* 84: 809, 1987). Under the physiological conditions, this glycosylation process is controlled by two T-cell factors which either enhance or inhibit this process. These factors are denominated glycosylation inhibiting factor (GIF) and glycosylation enhancing factor (GEF).

A unique property of GIF is its biochemical activity. This lymphokine binds to monoclonal antibodies against lipomodulin (a phospholipase inhibitory protein) and appears to be a phosphorylated derivative of a phospholipase inhibitory protein (Uede, et al., *J. Immunol.,* 130: 878, 1983). It was also found in the mouse that the major source of GIF is antigen-specific suppressor T-cells (Ts) (Jadieu, et al., *J. Immunol.,* 133: 3266, 1984). Subsequent experiments on ovalbumin (OVA)-specific suppressor T-cell hybridomas indicated that stimulation of the hybridoma cells with antigen (OVA)-pulsed syngeneic macrophages resulted in the formation of GIF that has affinity for OVA (antigen-binding GIF). However, the same hybridomas constitutively secreted GIF having no affinity for OVA (nonspecific GIF). Studies on the relationship between nonspecific GIF and OVA-binding GIF indicated that the antigen-binding GIF is composed of an antigen-binding polypeptide chain and a nonspecific GIF (Jadieu, and Ishizaka, in *Immune Regulation By Characterized Polypeptides*, Goldstein, et al., eds., Alan R. Liss, Inc., N.Y., p595, 1987). It was also found that the antigen-binding GIF shares common antigenic determinants with antigen-specific suppressor T-cell factors (TsF) described by the other investigators, and suppressed the antibody response in an antigen (carrier)-specific manner. Furthermore, not only antigen-binding GIF, but also antigen-specific TsF described by other investigators, bound to an immunosorbent coupled with monoclonal anti-lipomodulin (141-B9), and were recovered by elution of the immunosorbent at acid pH.

Despite the major limitations of desensitization in treating allergy, this technique continues to be the method of choice. Consequently, there is significant need for a technique which is antigen-specific yet does not have associated with it the side effects seen with existing desensitization regimens.

The suppression of the immune response is crucial in order to prevent host versus graft (HVG) and graft versus host rejection (GVH). Unfortunately, in the case of both autoimmune disease as well as in HVG and GVH, the immune response suppression uses highly toxic drugs which are of limited effectiveness and act systemically, rather than specifically. The severe limitations of such therapy point to the need for immunosuppressive agents which have less toxicity, but greater specificity.

An improved way to suppress an immune response to an antigen in a human would be to administer an immunosuppressively effective amount of human GIF which can specifically bind to the antigen. In so doing, the concentration of T suppressor factor is favored and, as a result, the immune response to the antigen is decreased. The present invention provides a means for accomplishing this result.

SUMMARY OF THE INVENTION

The inventor has substantially purified human antigen-specific GIF which suppresses the immune response to the homologous antigen. The human antigen-specific GIF, if desired, can be used therapeutically to suppress the human immune response to the antigen.

DETAILED DESCRIPTION OF THE INVENTION

The present invention relates to substantially pure human antigen-specific GIF with specificity for an antigen associated with an undesirable immune response. This human antigen-specific GIF is highly useful for the immunosuppression of the undesirable immune response in an antigen-specific manner.

Preferred in the present invention are human antigen-specific GIFs which can specifically bind allergens in an especially preferred embodiment of the invention, a human antigen-specific GIF is disclosed which binds to an epitope on phospholipase $A_2$($PLA_2$), the major allergen in honey bee venom. This specificity enables this antigen-specific GIF, and like antigen-specific GIFs with the same specificity, to be used to suppress the human immune response to $PLA_2$. In another especially preferred embodiment of the invention, a human antigen-specific GIF is disclosed which binds to an epitope on Japanese cedar pollen which can be used to suppress the human immune response to this antigen.

The teaching used to produce GIF with antigen-specificity to $PLA_2$ can be readily extended to other antigens by those of skill in the art to prepare and purify other GIF molecules with antigenic specificity for those other antigens without undue experimentation. As a consequence, the broad pioneering nature of the invention enables the preparation of human antigen-specific GIFs for other allergens which can be used to suppress such immune response mediated disorders as autoimmune disease and allergy. The production of various human antigen-specific GIFs is especially facilitated where the antigen of the undesirable immune response is known such as with most allergies and various autoimmune diseases.

The human $PLA_2$-specific GIF of the invention is obtained from, or has the identifying characteristics of, an antigen-specific GIF obtained from the cell line AC5 having ATCC accession number HB 10473. The human Japanese cedar pollen-specific GIF of the invention is obtained from, or has the identifying characteristics of, an antigen-specific GIF obtained from the cell line 31E9.

Methods of Producing and Characterizing Hybridomas

The general method used for production of hybridomas is well known (Kohler, et al., *European J. Imm.*, 6: 292, 1976). Briefly, peripheral blood mononuclear cells (PBMC) from a human allergic to honey bee venom were cultured in the presence of chemically modified $PLA_2$. Non-adherent cells were recovered and then cultured with IL-2 and lipocortin-1 prior to fusion with lymphoblastoid cell line BUC. Hybridomas were screened for production of human GIF specific for $PLA_2$.

More generally, the invention is directed to a method of producing a continuous hybridoma cell line which produces human antigen-specific GIF comprising:

(a) obtaining human antigen-primed T-cells which are activated to the antigen and cultured in the presence of IL-2 and phospholipase $A_2$ inhibitor; and (b) combining the activated T-cells by fusion with a fusion partner cell line to produce hybridomas capable of producing human antigen-specific GIF.

The antigen-primed T-cells can be obtained from any sample, including the mononuclear cell fraction of peripheral blood. The antigen-primed T-cells can then be activated by culturing in the presence of the antigen to which they have been primed, followed by expanding the activated T-cells in the presence of interleukin-2 (IL-2) and a phospholipase $A_2$ inhibitor. An especially useful phospholipase $A_2$ inhibitor for such purposes is lipocortin. Alternatively, synthetic compounds with $PLA_2$ inhibitory activity can be used such as 2-(p-amylcinnamoyl)-amino-4-chlorobenzoic acid, (ONO-RS-082; ONO Pharmaceutical Co.).

Under certain circumstances, such as where the primary antigen is toxic to the T-cells, it is desirable to chemically modify the antigen. Agents useful for such modification include guanidine HCl and cyanogen bromide, but those of skill in the art can easily ascertain similar agents without undue experimentation. Generally, it is preferred to use agents which do not destroy the external structure of the antigen, since it is thought that such external structures are important in suppressor T-cell epitopic recognition of the antigen. However, this issue is not significant for most antigens, such as many allergens, which are not cytotoxic. Consequently, with typical allergens, the native molecules can be used to stimulate the T-cells.

The present invention is directed to a method for generating antigen-specific human T-cells and T-cell hybridomas which produce human antigen-specific GIF, which are specifically reactive with an antigen which is associated with an immune response to be immunosuppressed.

The isolation of T-cell hybridomas producing a human antigen-specific GIF with the antigenic specificity of the human antigen-specific GIF of the invention can be accomplished using routine screening techniques to determine the elementary reaction pattern of the human antigen-specific GIF of interest. Thus, for example in the case of human GIF specific for $PLA_2$, if a human antigen-specific GIF being tested suppresses the immune response of cells from a patient allergic to $PLA_2$, then the human antigen-specific GIF being tested and the human GIF specific for $PLA_2$ produced by the hybridoma of the invention are equivalent.

Still another way to determine whether a human antigen-specific GIF has the specificity of a human antigen-specific GIF of the invention is to pro-incubate the human antigen-specific GIF of the invention with the antigen with which it is normally reactive (for example, bee venom $PLA_2$), and determine if the human antigen-specific GIF being tested is inhibited in its ability to bind the antigen. If the human antigen-specific GIF being tested is inhibited then, in all likelihood, it has the same epitopic specificity as the human antigen-specific GIF of the invention.

As used in this invention, the term "epitope" is meant to include any determinant capable of specific interaction with a human antigen-specific GIF or the monoclonal antibodies of the invention. Epitopic determinants usually consist of chemically active groupings of molecules such as amino acids or sugar side chains and usually have specific three dimensional structural characteristics, as well as specific charge characteristics.

In still another aspect, the invention relates to a method of producing substantially pure human antigen-specific GIF comprising:

(a) culturing a continuous hybridoma cell line capable of producing human antigen-specific GIF such that the cell line produces human antigen-specific GIF; and (b) isolating substantially pure human antigen-specific GIF from the culture.

The continuous hybridoma cell lines so used can themselves be produced as described above. In addition, during culturing the hybridoma cell line is preferably stimulated to produce human antigen-specific GIF by exposing the hybridoma cells to syngeneic macrophages which have been pulsed with the antigen to which the antigen-specific GIF binds, or with antibodies to the CD3 or T-cell receptor.

Various techniques can be used to isolate or substantially purify the human antigen-specific GIF from the culture. A particularly useful technique is affinity purification using the antigen, for example attached to a solid phase, to which the antigen-specific GIF binds. A modification of this technique is to use two affinity absorption steps, if desirable, to substantially purify the human antigen-specific GIF. In such a process, the step of isolating substantially pure human antigen-specific GIF includes:

(i) reacting the hybridoma cell line culture with a monoclonal antibody specifically reactive with human GIF;

(ii) eluting the human GIF from the monoclonal antibody;

(iii) reacting the eluted GIF with the antigen to which the human antigen-specific GIF binds;

(iv) eluting the human antigen-specific GIF from the antigen; and (v) recovering the human antigen-specific GIF.

Alternatively, the order of the two absorption steps can be reversed, wherein the step of isolating substantially pure human antigen-specific GIF includes:

(i) reacting the hybridoma cell line culture with the antigen to which the human antigen-specific GIF binds;

(ii) eluting the human GIF from the antigen;

(iii) reacting the eluted GIF with a monoclonal antibody specifically reactive with human GIF;

(iv) eluting the human antigen-specific GIF from the monoclonal antibody; and (v) recovering the human antigen-specific GIF.

Purification of human antigen-specific GIF is facilitated by adjusting the hybridoma cells to serum-free culture medium, such as ABC. After treatment of the subclone with anti-CD3, followed by culture of the hybridoma cells in Protein A-coated tissue culture dishes, antigen-binding GIF in culture supernatants can be purified by ion-exchange chromatography, described above. Under such conditions, the process of isolating substantially pure human antigen-specific GIF includes:

(i) contacting the hybridoma cell line culture 'supernatant with an anionic exchange matrix;

(ii) eluting the human GIF from the matrix;

(iii) reacting the eluted GIF with a monoclonal antibody specifically reactive with human GIF or with the antigen to which the human antigen-specific GIF binds, or both;

(iv) eluting the human antigen-specific GIF; and (v) recovering the human antigen-specific GIF.

Thus, ion-exchange chromatographic purification is used in combination with affinity-purification to isolate human antigen-specific GIF, for example, by using the antigen to which the antigen-specific GIF binds or by using an antibody specifically reactive with human GIF, or both, as described above.

In the preferred embodiment, DEAE (diethylaminoethyl) Sepharose is the matrix utilized for purification of antigen-specific human GIF. Other ion-exchange materials which can be utilized include virtually any of the commercially available anion exchange agaroses and celluloses, such as polysulfated agaroses, specifically including but not limited to QAE (quaternary amine) derivatives, ecteola (epichlorohydrintri-ethanolamine), TEAE (triethylaminoethyl) derivatives, and AE (amineethyl) cellulose. The specific parameters for binding and eluting from these various ion-exchange materials can be known to those of skill in the art, or can be readily ascertained, without undue experimentation.

When the hybridoma cell line culture supernatant is added to the anion-exchange matrix equilibrated with about 20 mM salt, e.g., NaCl, much of the GIF will pass through the column and the remainder are eluted with salt concentrations up to about 60 mM. Preferred for elution from DEAE are concentrations of NaCl from about 20 mM to about 60 mM contained in 10 mM Tris.

A monoclonal antibody which is particularly useful in the affinity purification of human GIF is the monoclonal antibody produced by a cell line $388F_1$ or monoclonal antibodies having the specificity of a monoclonal antibody produced by cell line $388F_1$.

THERAPEUTIC USES OF HUMAN ANTIGEN-SPECIFIC GIF

The term "suppressive" denotes a lessening of the detrimental effect of the undesirable immune response in the human receiving therapy. The term "immunosuppressively effective" means that the amount of human antigen-specific GIF used is of sufficient quantity to suppress the cause of disease or symptoms due to the undesirable immune response.

The dosage ranges for the administration of the human antigen-specific GIF of the invention are those large enough to produce the desired effect in which the symptoms of the immune response show some degree of suppression. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary from about 0.001 mg/kg/dose to about 2 mg/kg/dose, preferably about 0.001 mg/kg/dose to about 0.2 mg/kg/dose, in one or more dose administrations daily, for one or several days.

The human antigen-specific GIF of the invention can be administered parenterally by injection or by gradual perfusion over time. The human antigen-specific GIF of the invention can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also relates to a method for preparing a medicament or pharmaceutical composition comprising the human antigen-specific GIF of the invention, the medicament being used for therapy of an undesirable immune response to an antigen wherein the antigen is capable of binding by the human antigen-specific GIF of the invention.

The present invention is also directed to monoclonal antibodies, and B-cell hybridomas which produce them, which are specifically reactive with human GIF.

As stated above, techniques for production of hybridomas are well known to those of skill in the art. In brief, the B-cell hybridomas of the invention were prepared by immunizing BALB/c mice with affinity-purified human GIF and later boosted. Two weeks after the last immunization, spleen cells were obtained from the animals and transferred to syngeneic BALB/c mice which had been lethally irradiated. The syngeneic recipients were immunized twice with purified human GIF and 2 weeks after the last immunization the spleen cells were fused with SP 2/0-14AG myeloma cell line. Hybridomas were screened for monoclonal antibody production to human GIF.

The isolation of hybridomas producing monoclonal antibodies with the reactivity of the monoclonal antibodies of the invention can be accomplished using routine screening techniques to determine the elementary reaction pattern of the monoclonal antibody of interest. Thus, if a monoclonal antibody being tested reacts with human GIF, but does not react with mouse GIF, then the antibody being tested and the antibody produced by the hybridomas of the invention are equivalent.

The isolation of other hybridomas producing monoclonal antibodies with the specificity of monoclonal antibody $388F_1$, or any other monoclonal antibody of the invention, can be accomplished by one of ordinary skill in the art by producing anti-idiotypic antibodies (Herlyn, et al. *Science*, 232:100, 1986). An anti-idiotypic antibody is an antibody which recognizes unique determinants present on the monoclonal antibody produced by the hybridoma of interest. These determinants are located in the hypervariable region of the antibody. It is this region which binds to a given epitope and, thus, is responsible for the specificity of the antibody. The anti-idiotypic antibody can be prepared by immunizing an animal with the monoclonal antibody of interest. The animal immunized will recognize and respond to the idiotypic determinants of the immunizing antibody by producing an antibody to these idiotypic determinants. By using the anti-idiotypic antibodies produced by the second animal, which are specific for the monoclonal antibodies produced by a single hybridoma which was used to immunize the second animal, it is now possible to identify other clones with the same idiotype as the antibody of the hybridoma used for immunization and thereby greatly simplify and reduce the amount of screening needed to find other hybridomas producing monoclonal antibodies with the specificity of the monoclonal antibodies of the invention.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

Alternatively, it is possible to evaluate, without undue experimentation, a monoclonal antibody to determine whether it has the same specificity as $388F_1$ of the invention by determining whether the monoclonal antibody being tested prevents $388F_1$ from binding to a particular antigen, for example human GIF, with which $388F_1$ is normally reactive. If the monoclonal antibody being tested competes with $388F_1$, as shown by a decrease in binding by $388F_1$, then it is likely that the two monoclonal antibodies bind to the same epitope.

Still another way to determine whether a monoclonal antibody has the specificity of $388F_1$ is to pro-incubate $388F_1$ with an antigen with which it is normally reactive, for example, human GIF, and determine if the monoclonal antibody being tested is inhibited in its ability to find the antigen. If the monoclonal antibody being tested is inhibited then, in all likelihood, it has the same epitopic specificity as the monoclonal antibody of the invention.

Under certain circumstances, monoclonal antibodies of one isotype might be more preferable than those of another in terms of their diagnostic or therapeutic efficacy. Particular isotypes of a monoclonal antibody can be prepared either directly, by selecting from the initial fusion, or prepared secondarily, from a parental hybridoma producing monoclonal antibody of different isotype, by using the sib selection technique to isolate class-switch variants (Steplewski, et al., *Proceedings of National Academy of Sciences, USA*, 82: 888653, 1985; Spira, et al., *Journal of Immunological Methods*, 74: 307, 1984). Thus, the monoclonal antibodies of the invention would include class-switch variants having the specificity of monoclonal antibody $388F_1$ which is produced by ATCC HB 10472. This cell line was placed on deposit for 30 years at the American Type Culture Collection (ATCC) in Rockville, Md. prior to Jun. 4, 1990.

The term "antibody" as used in this invention is meant to include intact molecules as well as fragments thereof, such as, for example, Fab and F(ab₁)₂, which are capable of binding the epitopic determinant.

The monoclonal antibodies of the invention can also be used in immuneaffinity chromatography for the purification of the various types of human GIF mentioned herein. One way by which such immunoaffinity chromatography can be utilized is through the use of, for example, the binding of the monoclonal antibodies of the invention to CNBr-Sepharose-4B or Tresyl-activated Sepharose (Pharmacia). These solid phase-bound monoclonal antibodies can then be used to specifically bind human GIF from mixtures of other proteins to enable its isolation and purification. The bound IFN-gamma can be eluted from the affinity chromatographic material using techniques known to those of ordinary skill in the an such as, for example, chaotripic agents, low pH, or urea.

The above disclosure generally describes the present invention. A more complete understanding can be obtained by reference to the following specific examples which are provided herein for purposes of illustration only, and are not intended to limit the scope of the invention.

EXAMPLE 1

PREPARATION OF HYBRIDOMA CELL LINES PRODUCING HUMAN ANTIGEN-SPECIFIC GLYCOSYLATION INHIBITING FACTOR (GIF) AND PURIFICATION TECHNIQUES

A. ANTIGENS

Lyophilized phospholipase A₂(PLA₂) from bee venom was purchased from Sigma Chemical Co., St. Louis, Mo. Denatured PLA₂ (-PLA₂) and cyanogen bromide-treated PLA₂ were prepared by the method described by King, et al., *Arch. Biochem and Biophys.*, 172: 661, 1976. For the preparation of D-PLA₂, 5 mg of PLA₂ were dissolved in 0.1M Tris HCl buffer, pH 8.6, and denatured in 6M guanidine HCl in the presence of 5 mg/ml dithiothreitol. After 18 hours at room temperature, sulfhydryl groups were carboxymethylated with iodoacetic acid. The denatured protein was dialyzed against 0.02M acetic acid and kept at −40° C. until use. For the cleavage of methionine bonds in PLA₂, 10 mg bee venom PLA₂ was dissolved in 0.4 ml distilled water, and 1.2 ml formic acid containing 100 mg CNBr were added. After 2 hours at room temperature, the mixture was diluted two-fold with H₂O and lyophilized in Speed Vac. Native PLA₂ was coupled to Tresyl activated Sepharose (Pharmacia) following the procedures recommended by the manufacturer. Unless otherwise stated, 1 mg protein was coupled to 1 ml Sepharose.

B. ANTIBODIES

Purified human E myeloma protein PS, monoclonal mouse IgE from the hybridoma H-1 DNP-E-26 (Liu, et al., *J. Immunol.*, 124: 2728, 1980) and monoclonal anti-CD3 (OKT 3) were the same preparations as those described in a previous article (Carini, et al., *J. Immunol. Methods*, 127: 221, 1990). Ascitic fluid containing the monoclonal anti-T-cell receptor αβ, WT 31 C, (Spits, et al., *J. Immunol.*, 135: 1922, 1985) was kindly supplied by Dr. J. DeVries, DNAX Institute of Molecular and Cellular Biology, Palo Alto, Calif. The mouse monoclonal antibody against rabbit lipomodulin 141 B9 (Iwata, et al., *J. Immunol.*, 132: 1286, 1984) was the same preparation as that described in a previous article (Askasaki, et al., *J. Immunol.*, 131: 3172, 1986). Specifically-purified goat antibodies against mouse IgG, which contained both anti-heavy (γ) chain and anti-light chain, were previously described (Suemura, et al. *J. Immunol.*, 125: 148, 1980). Fluoresceinated goat anti-mouse IgG antibodies were purchased from Cappel. Human IgE and anti-lipomodulin antibody (141B9) were coupled to CL-Sepharose 4B; approximately 5 mg of protein were coupled to 1 ml Sepharose.

C. CELL LINES

RPMI 8866 lymphoblastoid cells were cultured in RPMI 1640 medium enriched with 10% fetal calf serum, 2 mM L-glutamine, 50 μM 2-mercaptoethanol and antibiotics (RPMI 1640 culture medium). The mouse T-cell hybridoma 12H5 cells (Iwata, et al., *J. Immunol.*, 140: 2534, 1988) were maintained in high glucose Dulbecco's modified Eagle's medium (DMEM) described in a previous article (Huff, et al., *Proc. Natl. Acad. Sci., USA*, 129: 509, 1982). A hypoxanthine guanine phosphoribosyltransferase-deficient mutant of the human lymphoblastoid cell line CEM (BUC) cells were previously described (Huff & Ishizaka, *Proc. Natl. Acad. Sci., USA*, 81: 1514, 1984).

D. CELL CULTURE AND CONSTRUCTION OF HYBRIDOMAS

Peripheral blood was obtained from a patient allergic to honey bee venom, and mononuclear cells of the blood (PBMC) were obtained by centrifugation on Ficoll-Pague (Pharmacia). To activate antigen-primed T-cells, PBMC were suspended in RPMI 1640 culture medium at the concentration of 3×10⁶ nucleated cells/ml, and cultured for three days in the presence of 10 μg/ml D-PLA₂ or CNBr-treated PLA₂. Non-adherent cells were recovered, resuspended in fresh culture medium (2×10⁵ cells/ml), and then cultured for four days with 60 units/ml purified IL-2 (chromatographically purified human IL-2, Electro-nucleonics, Silverspring, Md.), in the presence of 3 μg/ml recombinant human lipocortin 1, which was kindly supplied by Drs. J. Browning and B. Pepinsky, Biogen.

To construct T-cell hybridomas, 1.2'10⁷ T-cells, which had been propagated by IL-2, were mixed with twice the number of BUC cells. Mixed cells were pelleted together and fused by using polyethylene glycol (1300–1600 MW., Sigma). Detailed procedures for cell fusion were as previously described (Huff, et al., *Proc. Nat'l. Acad. Sci., U.S.A.* 81: 1514, 1984). Cells were resuspended in hypoxanthine/aminopterin/thymidine (HAT)-containing DMEM, and 5×10⁴ cells were seeded in each well of 96 well plates. Hybrid clones were maintained in complete DMEM with biweekly subcultures. In order to stimulate the T-cell hybridomas, the cells were treated with 8 μg/ml OKT 3 for 40 minutes at 0° C., and the antibody-treated cells (1×10⁶/ml) were seeded in Limbro tissue culture wells (Flow Labs, McLean, Va.) which had been coated with 10 μg/ml anti-MGG. Culture supernatants were obtained after 24 hour culture.

E. DETECTION OF CD3 AND TcR

The hybridoma cells (1×10⁶/sample) were incubated 40 minutes at 0° C. with 8 μg/ml OKT 3 or a 1:1000 dilution of anti-TcRαβ(WT31)-containing ascitic fluid in RPMI 1640 medium supplemented with 5% FCS and 10 μM NaN3. As controls, aliquots of the same cells were treated with the same concentration of mouse IgG₂ₐ. (Becton-Dickinson, isotype control). Cells were washed twice with PBS containing 5% FCS, and then incubated with fluoresceinated anti-mouse IgG for 40 minutes. After washings, cell-associated fluorescence was analyzed by using FACScan from Becton-Dickinson.

The CD3⁺ hybridoma cells were identified by resetting using ox erythrocytes coated with anti-mouse IgG. The antibodies were coupled to erythrocytes by the method of Wilhelm, et al., (*J. Immunol. Methods*, 90: 89, 1986).

Briefly, 0.5 ml of packed ox erythrocytes were washed 4 times with saline, and resuspended in 0.75 ml of 0.5 µg/ml purified anti-MGG; 25 µl of $CrCl_3$ (16.5 mg $CrCl_3$ dissolved in 5 ml saline) were added to the cell suspension under gentle mixing, and the cell suspension was incubated for 1 hour at 30° C. The anti-MGG-coupled erythrocytes were washed 4 times with saline arid resuspended in 5 ml FCS (approximately $1 \times 10^9$ erythrocytes/ml). To detect the $CD3^+$ cells, pellets of $10^6$ hybridoma cells were suspended in 80 µl of DPBS containing 5% FCS and 8 µg/ml OKT 3. After 45 minutes at 0° C., the cells were washed twice and resuspended in 80 µl DPBS-5% FCS, and 20 µl of a suspension of anti-MGG-coated erythrocytes and crystal violet were added to the cell suspension. The mixtures were centrifuged at 200 g for 5 minutes and tubes were incubated for 2 hours at 0° C. The pellets were gently resuspended and examined for rosetting cells under microscope.

F. ENRICHMENT OF $CO3^+$ CELLS

Hybridoma cells treated with 8 µg/ml OKT 3 ($1.5 \times 10^6$ cells) were mixed with anti-MGG coupled erythrocytes (ca $4 \times 10^8$ erythrocytes) to form rosettes by the procedures described above. Pellets were resuspended and applied to the top of Percoll gradient consisting of 60% and 50% Percoll layers. Tubes were centrifuged for 20 minutes at 1200 RPM (700 g) at room temperature. The pelleted cells were washed twice with culture medium, and the erythrocytes were lysed by treatment with 0.83% $NH_4Cl$ buffer for 1 minute at 0° C. The cells were washed with and resuspended in DME culture medium and cultured to expand the cell population.

Further enrichment of $CD3^+$ cells was carried out by cell sorting. Hybridoma cells were treated with OKT 3 and stained with fluoresceinated anti-MGG. The positively stained cells were selected by sorting the cells by using FACSTAR (Becton-Dickinson).

G. PURIFICATION AND DETECTION OF IgE-BF

Culture supernatant of T-cell hybridomas were filtered through Diaflo YM 100 membranes (Amicon Corp., Lexington, Mass.) and the filtrates were concentrated tenfold by ultrafiltration through YM5 membranes. IgE-BF in the filtrates were purified by using IgE-coupled Sepharose by the described procedures (Ishizaka & Sandberg, *J. Immunol.*, 125:1692, 1981). The presence of IgE-BF in culture filtrates or acid eluate fraction from IgE-Sepharose was assessed by inhibition of rosette formation of $FceR^+B$ lymphoblastoid cell line. RPMI 8866 cells with human IgE-coated ox erythrocytes (E-IgE) by the procedures previously described (Kisaki, et al., *J. Immunol.*, 138: 3345, 1987). The proportion of rosette forming cells (RFC) in 300 RPMI 8866 cells was determined in triplicate and was expressed as the average ±SD.

Rodent IgE-BF formed by the 12H5 cells were detected by the same procedure, except that rat IgE-coated ox erythrocytes were employed as indicator cells, and mesenteric lymph node cells of Lewis strain rate infected with Nippor-tronngylus brasitiensis were used as a source of FceR+B cells (Yodoi & Ishizaka, *J. Immunol.*, 124:1322, 1980).

H. DETECTION OF GIF

GIF was detected by using T-cell hybridoma 12H5 cells (Iwata, et al., *J. Immunol.*, 140: 2534, 1988). A suspension of the hybridoma cells was mixed with an equal volume of a test sample, and the cell suspensions were cultured for 24 hours with 10 µg/ml mouse IgE. Culture supernatants were filtered through CF50A membranes, and filtrates containing IgE-BF were fractionated on lentil lectin Sepharose (Yodoi, et al., *J. Immunol.*, 125: 1436, 1980). Both unbound proteins (effluent fraction) anti those eluted with 0.2 M α methylm-annoside (eluate fraction) were assessed for the presence of IgE-BF by rosette inhibition technique. When the 12H5 cells were cultured with mouse IgE alone, essentially all IgE-BF formed by the cells bound to lentil lectin Sepharose and were recovered by elution with α methylmannoside. Thus, the ratio of the percent rosette inhibition between the effluent/eluate fraction is less than 0.2. If a sufficient amount of GIF were added to the culture of 12H5 cells together with mouse IgE, the majority of IgE-BF formed by the cells lacked affinity for lentil lectin and were recovered in the effluent fraction (Iwata & Ishizaka, *J. Immunol.* 141: 3270, 1988). Thus, GIF was taken as (+), if the ratio of the percent rosette inhibition between the effluent/eluate fraction were 3.0 or higher.

I. FRACTIONATION OF GIF

In order to determine whether GIF from hybridomas has affinity for bee venom $PLA_2$, culture filtrates of hybridoma cells were fractionated an antigen-coupled Sepharose. Hybridoma cells were treated with OKT 3 antibody (8 µg/ml) and 8 ml aliquots of the antibody treated or untreated cell suspension ($1.5 \times 10^6$ cells/ml) were cultured in anti-MGG-coated tissue culture flasks. Culture supernatants were concentrated four-fold, and a 2 ml sample was absorbed with 0.4 ml IgE-Sepharose. The effluent fraction was mixed with 0.5 ml $PLA_2$-Sepharose overnight, and immunosorbent was packed into a small column. After effluent fraction was recovered, the column was washed with DPBS, and then eluted with 1.0 ml glycine HCl buffer, pH 3.0. Partial purification of GIF on anti-lipomodulin (14189) Sepharose was carried out by the procedures previously described (Akasaki, et al., *J. Immunol.*, 136: 3172, 1987).

J. DETERMINATION OF PHOSPHOLIPASE INHIBITORY ACTIVITY

Affinity-purified GIF was treated with alkaline phosphatase as previously described (Uede, et al., *J. Immunol.*, 139: 898, 1983). Briefly 1 ml of the preparation was dialyzed against Tris-HCl buffer, pH 8.2 and was mixed with 1 unit of insoluble alkaline phosphatase (calf intestinal, Sigma) for 2 hours at room temperature. After centrifugation, the supernatant was dialyzed against 0.1M Tris-HCl buffer, pH 8.0. Phospholipase $A_2$ inhibitory activity of the alkaline-phosphatase treated samples was determined using *E coli* which were biosynthetically labeled with $^3H$-oleic acid and porcine pancreatic $PLA_2$ (Sigma) (Rothut, et al., *Biochem. Biophys. Res. Commun.*, 117: 878, 1983). Detailed procedures were described in Ohno, et al. (Internat. Immunol., 1: 425, 1989). Briefly, porcine pancreatic $PLA_2$ ($1 \times 10^{-5}$ units) was mixed with GIF in a total volume of 150 µl. After 5 minutes at 25° C., 50 µl of a suspension of $^3H$-labeled *E coli* (5000 cpm) was added, and the mixtures were incubated for 5 minutes at 25° C. The reaction was stopped by the addition of 50 µl 2M HCl, and 50 µl of 100 mg/ml BSA was added to the mixtures. The suspensions were centrifuged for 1 minute at 5500 g, and radioactivity in 250 µl of supernatant was measured in a scintillation spectrometer.

K. ION EXCHANGE COLUMN CHROMATOGRAPHY

Culture supernatant of AC5 cells in serum-free medium was concentrated 25 to 100 fold by ultrafiltration. After centrifugation at 10,000 rpm for 20 min, the supernatant was diluted 8-fold with distilled water, adjusted to pH 8.0 with Tris, and immediately applied to a DEAE-Sepharose CL-6B (Pharmacia) column (3 ml volume) which was equilibrated with 10 mM Tris HCl buffer, pH 8.0. After effluent (passed-through) fraction was recovered, the column was washed with 4 column volumes of 10 mM Tris-HCl buffer containing 20 mM NaCl, and the washing was combined to the passed through fraction. Proteins bound to the column were eluted successively with 4 column volumes of 10 mM Tris HCl buffer, pH 8.0 containing 50 mM, 75 mM, 100 mM, 150 mM, and 200 mM NaCl. Each eluate fraction was concentrated and dialyzed against Dulbecco's phosphate buffered saline (DPBS).

L. GEL FILTRATION

One ml sample in DBPS was applied to a Superose 12 column (1.6×50 cm, Pharmacia), connected to HPLC (Beckman, System Gold). Proteins were eluted from the column with DPBS at a flow rate of 1 ml/min, and appropriate fractions were collected. The column was calibrated with human IgE (PS protein, MW: 185,000), bovine serum albumin (BSA, MW: 67,000), ovalbumin (MW: 43,000), soybean trypsin inhibitor (MW: 20,100), and cytochome C (MW: 12,500). All standard proteins except IgE were obtained from Sigma. Retention time for the standard proteins were 41.97, 52.08, 55.135, 62.097, and 71.67 min, respectively.

M. AFFINITY-PURIFICATION OF GIF

Culture supernatant of CL3 clone in complete DME medium was concentrated 5-fold by ultrafiltration, and GIF in the supernatant was absorbed to 141B9-Sepharose or anti-GIF Sepharose by recycling the supernatant overnight through the immunosorbent column (5 ml volume) (Iwata, et al., *J. Immunol.*, 141:3270, 1988). The immunosorbent was washed with 20 column volumes of DPBS, and proteins bound to the beads were recovered by elution with 0.1 M glycine HCl buffer, pH 3.0. Murine GIF from the 231F1 cells was purified by the same technique using the 141B9-Sepharose.

In order to isolate GIF in culture supernatant of AC5 cells in protein-free medium, the supernatant was concentrated 50 to 100-fold by ultrafiltration. An appropriate fraction of the supernatant from a DEAE-Sepharose column was concentrated to 5–6 ml and mixed overnight at 4° C. with 1.0 to 1.5 ml of Affigel 10-immunosorbent coupled with monoclonal anti-GIF antibody. The suspension was packed into a small column and the immunosorbent was washed with 40 column volumes of DPBS. In some experiments, the immunosorbent was washed with 40 column volumes of DPBS and 20 column volumes of PBS containing 0.5M NaCl Proteins bound to the immunosorbent were eluted with 0.05M glycine HCl buffer containing 0.15M NaCl, pH 3.0–3.2.

N. DETECTION OF GIF BY SDS-PAGE

Affinity-purified GIF was dialyzed against 0.01% SDS in deionized water, and lyophilized in a Speed vac (Savant Instruments, Hicksville, N.Y.). Samples were then analyzed by SDS gel electrophoresis in 15% polyacrylamide slab gel by using the Laemmli system (Laemmli, U.K., *Nature*, 227:680, 1970). Gels were fixed and protein bands were detected by silver staining (Ochs, et al., *Electrophoresis*, 2:304, 1981). Molecular weight standards were obtained from Pharmacia.

O. ELISA ASSAYS

In order to detect monoclonal anti-GIF antibody, the method described by Steele, et al. (*J. Immunol.*, 142:2213, 1989) was employed with slight modifications. Briefly, Immulon I plates (Dynatech) were coated overnight with 100 µl of affinity-purified GIF diluted with 0.1M carbonate coating buffer, pH 9.6. Plates were washed 3 times with phosphate buffered saline (PBS) containing 0.05% Tween 20 between each of the following steps. Plates were blocked with 2% BSA in PBS for 6–9 hours. One hundred microliters of each test sample was then added to the well, and plates were kept overnight at 4° C. Binding of mouse Ig to the plate was detected by using alkaline phosphatase-coupled goat anti-mouse Ig (Zymed Lab, So. San Francisco, Calif.) and alkiline phosphatase substrate (Sigma). ELISA signal was read in a microplate reader MR 5000 (Dynatech Lab) with a 410 nm filter 30 rain after the addition of substrate. Isotype of monoclonal antibodies was determined with ELISA assay by using an isotyping kit for mouse mAb (Zymed Lab).

For the detection of GIF in fractions of an affinity-purified GIF preparation, a biotin-avidin system and amplification method (Stanley, et al., *J. Immunol. Methods*, 83:89, 1985) were employed to increase the sensitivity. Maxi-Sorp microtiter plates (Nunc, Copenhagen, Denmark) were coated with 50 µl of each fraction. After incubation for 2 hours at 37° C., plates were washed with Tween/PBS and blocked with 2% BSA overnight at 4° C. After washing, 50 µl of biotin-coupled mAb 141-B9 (200 ng/ml) were added to each well and the plate was incubated for 2 hours at 37° C. The plate was washed and 50 µl of a 1:1500 dilution of streptavidin-alkaline phosphatase conjugate (Zymed Lab) were added to each well. After incubation for 1 hour at 37° C., quantities of alkaline phosphatase bound to the wells were measured by amplification system (Stanley, et al., *J. Immunol. Methods*, 83:89, 1985), (GIBCO-BRL, Bethesda, Md.). ELISA signal was determined at 490 nm.

EXAMPLE 2

CHARACTERIZATION OF HYBRIDOMAS PRODUCING HUMAN ANTIGEN-SPECIFIC GIF

As described above, PBMC of a bee venom-sensitive patient were cultured for three days in the presence of 10 µg/ml D-PLA$_2$, and activated T-cells were propagated by IL-2 for four days in the presence of 3 µl/ml recombinant lipocortin. T-cells were then fused with BUC cells to construct hybridomas. In this experiment, 4 hybridoma clones were obtained. Each hybridoma clone was cultured in complete DMEM and culture supernatants were filtered through YM100-membranes. Filtrates were concentrated ten-fold and assessed for the presence of GIF by using the 12H5 cells. The results shown in Table I indicate that two of the four hybridoma clones constitutively secrete GIF.

TABLE I

Selection of GIF-Producing Hybridomas

| Hybridoma | GIF Activity[a] Effluent/Eluate | $^3$H-Oleic Acid Release[c] | |
|---|---|---|---|
| | | Release (cpm) | Inhibition (%) |
| Cl 1 | 0/26 (−) | ND | — |
| Cl 2 | 2/33 (−) | 390 ± 27 | 4 |
| Cl 3 | 29/0 (+) | 257 ± 25 | 37 |
| Cl 7 | 27/5 (+) | 303 ± 17 | 26 |
| Control | 0/31[b] | 408 ± 15 | — |

[a]Culture filtrates of each clone were concentrated ten-fold. One volume of the filtrate was added to an equal volume of a suspension of the 12H5 cells, and the cells were cultured for 24 hours in the presence of 10 µg/ml mouse IgE. Numbers in the column represent the percent of rosette inhibition by the effluent/eluate fractions from lentil lectin Sepharose. The proportion of IgE-RFC in the absence of IgE-BF was 24.4 ± 0.3 (SD) %.
[b]The 12H5 cells were cultured with 10 µg/ml mouse IgE alone, and IgE-BF in culture filtrates were fractionated on lentil lectin Sepharose.
[c]Culture filtrates were fractionated on 141B9-Sepharose, and acid eluates from the immunosorbent were concentrated to 1/100 volume of the original culture supernatant. The samples were treated with alkaline phosphatase, and dephosphorylated materials were assessed for the ability to inhibit pancreatic phospholipase A2.

The presence of CD3 determinants on the hybridoma clone CL3 was assessed by fluorocytometry and the rosetting technique. The cells were treated with 8 µg/ml monoclonal antibody OKT3 and then stained with fluoresceinated goat anti-mouse Ig. Less than 10% of the total cells were stained. It was also found that only 6–8% of the OKT3-treated cells formed rosettes with anti-MGG-coupled erythrocytes. As a consequence, the $CD3^+$ cells were enriched using the rosetting procedures described in Example 1. Cells which formed rosettes with anti-MGG coupled erythrocytes were separated from non-rosetting cells by density gradient centrifugation on Percoll layers and were expanded by culture in complete DMEM. The same procedures were repeated three times to enrich the $CD3^+$ cell population. Treatment of the final cell preparation with OKT3 antibody followed by incubation with anti-MGG-coated erythrocytes showed that 80–90% of the cell population formed rosettes..Approximately 75% of the cells were stained by OKT3 in cytofluorometry. However, when culture of the cells for 2 weeks with four passages resulted in the decline of $CD3^+$ cells to approximately 52% (as determined by cytofluorometry), the $CD3^+$ cell population was further enriched by cell sorting and expanding the cells by culture. After repeating the cell sorting twice, a CL3 population was obtained which stably expressed CD3. Fluorescent staining of the population with OKT3 and WT31 (anti-TcRαβ) indicated that essentially 100% of the cells expressed CD3 and the majority of the cells expressed TcRαβ. The $CD3^+$ cell population and $CD3^-$ population were cultured and culture filtrates were assessed for the presence of GIF by using the 12H5 cells. The GIF activity was detected in culture filtrates of $CD3^+$ cells, but not in the culture filtrates of $CD3^-$ population. The results indicated that the source of GIF is $CD3^+$cells.

Since one of the unique properties of mouse GIF is that the monoclonal anti-lipomodulin (141B9) binds the lymphokine, it was decided to determine whether human GIF from the CL3 cells would be absorbed with 141B9-coupled Sepharose. The $CD3^-$, CL3 clone was cultured to yield 1 liter of culture supernatant. After filtration through a YM100 membrane, the filtrates were concentrated to 5 ml, and fractionated on 1 ml 141-B9 Sepharose. After recovering the effluent fraction, the immunosorbent was washed with 10 column volumes of DPBS, and then eluted with 5 column volumes of glycine-HCl buffer, pH 3.0. After dialysis against DPBS, distribution of GIF activity in the fractions was determined by using the 12H5 cells. The results shown in Table II indicate that essentially all GIF activity in the culture filtrate bound to 141-B9 Sepharose and was recovered by elution at acid pH.

TABLE II

Human GIF From CL3 Clone Purified By Affinity Chromatography On Anti-Lipomodulin Sepharose[a]

| Fraction from 141B9-Sepharose[b] | Dilution | GIF Activity[c] Effluent/Eluate |
|---|---|---|
| Effluent | 1:10 | 0/31 (−) |
| Washing | 1:10 | 0/35 (−) |
| Eluate | 1:10 | 42/0 (+) |
|  | 1:40 | 45/0 (+) |
|  | 1:80 | 39/0 (+) |
| Media Control | — | 0/34 |

[a]Culture supernatants of the CL3 clone were filtered through YM100 membranes, and filtrates were concentrated 200-fold. 5 ml of the concentrated filtrate was fractionated on 1 ml 141B9-Sepharose.
[b]After recovering the effluent fraction, the immunosorbent was washed with 5 column volumes of DPBS, and then eluted with 5 column volumes of glycine HCl buffer, pH 3.0.

TABLE II-continued

Human GIF From CL3 Clone Purified By Affinity Chromatography On Anti-Lipomodulin Sepharose[a]

| Fraction from 141B9-Sepharose[b] | Dilution | GIF Activity[c] Effluent/Eluate |
|---|---|---|

[c]GIF activity was assessed by using the 12H5 cells by the same procedures described in Table I. Numbers in the column represent percent rosette inhibition by the effluent/eluate fractions from lentil lectin Sepharose. The proportion of IgE-RFC in the absence of IgE-BF was 22.9 ± 0.6 (SD) % in this assay. (+) indicated the presence of GIF.

Previous experiments provided evidence that murine GIF is a phosphorylated derivative of a phosphotipase inhibitory protein (Uede, et al., *J. Immunol.*, 139: 898, 1983). Thus, GIF in the culture filtrates of CL3 clone was purified by using the 141 B9-Sepharose. Culture filtrate of the three other clones, CL1, CL2, and CL7 were fractionated on the 1 41 B9-Sepharose in a similar manner. The acid eluates from the immunosorbent were treated with alkaline phosphatase, and assessed for the ability to inhibit the release of $^3$H-oleic acid from biosynthetically labeled *E. coli* by pancreatic phospholipase $A_2$ (Rothut, et al., *Biochem. Biophys. Res. Commun.*, 117: 878, 1983). The results included in Table I indicate that the affinity-purified GIF from CL3 and CL7 exerted phospholipase inhibiting activity, while the same fraction from CL1 and CL2, failed to inhibit phospholipase $A_2$.

EXAMPLE 3

ANTIGEN-BINDING PROPERTIES OF GIF

Previous experiments have shown that antigen-activated T-cells propagated with IL-2 in the presence of lipocortin constitutively released GIF that had no affinity for bee venom $PLA_2$, but cross-linking of CD3 on the same cells resulted in the formation of GIF having affinity for the antigen-coupled Sepharose together with IgE-BF. In view of these findings, it was decided to determine whether the CL3 clone produces antigen-binding GIF and IgE-BF. The cells were treated with OKT3 at 0° C., and the antibody-treated cells (1.5×10$^6$ cells/ml) were cultured in the anti-MGG-coated cells. As a control, untreated CL3 cells were cultured in the anti-MGG-coated wells. Culture supernatants were filtered through YM100 membranes and concentrated sevenfold by ultra-filtration. The concentrated culture filtrates were absorbed overnight with 1 ml IgE-Sepharose, and unbound protein fraction and 2 ml of washings were combined. The IgE-Sepharose was thoroughly washed, and eluted with glycine HCl buffer. The eluate fractions from IgE-Sepharose were assessed for the presence of IgE-BF by using RPMI 8866 cells as the source of FcεR$^-$ cells.

TABLE III

Failure Of The GIF From The CL3 Clone To Bind To Bee Venom $PLA_2$

| Treatment[a] | IgE-BF[b] (%) | GIF Activity In $PLA_2$-Sepharose[c] | | |
|---|---|---|---|---|
| | | Eluate | Washing | Eluate |
| OKT 3 | 23 | 34/0 (+) | 21/0 (+) | 0/24 (−) |
| None | 0 | 28/0 (+) | 22/13 (±) | 0/26 (−) |

[a]Untreated or CD3-treated cells were cultured in anti-MGG-coated wells.

TABLE III-continued

Failure Of The GIF From The CL3 Clone To Bind To Bee Venom $PLA_2$

| | | GIF Activity In $PLA_2$-Sepharose[c] | | |
|---|---|---|---|---|
| Treatment[a] | IgE-BF[b] (%) | Eluate | Washing | Eluate |

[b] 30 ml culture supernatant were filtered through YM100, and filtrates were concentrated to 4 ml. The samples were absorbed with 1.0 ml IgE-Sepharose. Acid eluate fraction was adjusted to 4.0 ml and assessed for IgE-BF by rosette inhibition. The proportion of IgE-BF in the absence of IgE-BF was 37.7 ± 1.0%.

[c] 1.0 ml of the effluent fraction from IgE-Sepharose was fractionated on $PLA_2$-Sepharose. The effluent, washing and acid eluate fractions were adjusted to 1.3 ml, and were assessed for GIF activity by using the 12H5 cells. Numbers in the column represent percent rosette inhibition by the effluent/eluate fractions from lentil lectin Sepharose. The proportion of IgE-RFC in the absence of IgE-BF was 21.7 ± 0.6 (SD) %.

The results shown in Table III indicate that anti-CD3-treated cells formed IgE-BF, while untreated cells failed to produce a detectable amount of IgE-BF. The effluent fraction from IgE-Sepharose was concentrated two-fold and 1 ml samples were fractionated on 0.25 ml $PLA_2$-Sepharose. The effluent fraction, washing, and eluate fraction were adjusted to 1.5 ml, and the samples assessed for GIF activity. As shown in Table III, GIF from both unstimulated and anti-CD3 treated cells failed to bind to $PLA_2$-Sepharose.

It was thought that the failure of the GIF from anti-CD3 treated CL3 cells to bind $PLA_2$ might be related to the use of $D-PLA_2$ for the activation of T-cells. In order to investigate this possibility, more T-cell hybridomas from PBMC of a bee venom sensitive patient were constructed. The protocol for the construction of T-cell hybridomas was exactly the same as that described above, except that PBMC were stimulated with 10 µg/ml CNBr-treated $PLA_2$ instead of $D-PLA_2$. As the results of this experiment, 22 hybridoma clones were obtained. The GIF assay of culture filtrates of each clone indicated that 10 out of 22 clones constitutively formed GIF (results not shown). Seven GIF-secreting clones were treated with OKT3 and the antibody-treated cells were cultured in anti-MGG-coated dishes. Culture filtrates were concentrated four-fold and absorbed with IgE-Sepharose.

TABLE IV

Formation Of Antigen-Binding GIF By Anti-CD3-Treated Hybridoma Cells[a]

| | | GIF Activity in $PLA_2$-Sepharose[c] | |
|---|---|---|---|
| Clone | IgE-BF[b] (%) | Effluent | Eluate |
| AC5 | 20 | 0/21 (−) | 31/0 (+) |
| AF10 | 36 | 19/0 (+) | 0/21 (−) |
| BA6 | 8 | 29/0 (+) | 0/24 (−) |
| BE12 | 65 | 0/31 (−) | 25/0 (+) |
| BF5 | 65 | 0/27 (−) | 20/0 (+) |
| CB7 | 64 | 0/28 (−) | 17/0 (+) |
| CE5 | 58 | 0/28 (−) | 35/0 (+) |

[a] $1.2 \times 10^7$ cells were treated with OKT 3. Cells were resuspended in 8 ml culture medium and seeded in an anti-MGG-coated flask. Culture supernatant were concentrated four-fold and absorbed with IgE-Sepharose. Effluents from IgE-Sepharose were then fractionated on $PLA_2$-Sepharose and GIF activity in the effluent and eluate fraction was determined.

[b] Acid eluate fractions from IgE-Sepharose were assessed for the presence of IgE-BF. The proportion of IgE-RFC in the absence of IgE-BG was 26.3 ± 0.6 (SD) %.

[c] GIF activity was determined by using the 12H5 cells. Numbers represent the percent rosette inhibition by the effluent/eluate fractions from lentil lectin Sepharose. Proportion of IgE-RFC in the absence of IgE-BF was 26.0 ± 0.7 (SD) %. (+) indicates the presence of GIF.

As shown in Table IV, acid eluate fraction from IgE-Sepharose of 6 out of 7 clones contained detachable amounts of IgE-BF. The effluent fractions from IgE-Sepharose were then fractionated on $PLA_2$-Sepharose, and the effluent and eluate fractions from the immunosorbent were assessed for GIF activity. The results shown in Table IV indicate that the majority of GIF from 5 out of 7 clones bound to $PLA_2$-Sepharose and recovered by elution at acid pH. In order to confirm that cross-linking of CD3 is required for these clones to produce antigen-binding GIF, the 5 clones were cultured in anti-MGG-coated cells without treatment with anti-CD3. As expected, culture supernatants did not contain IgE-BF, and GIF in the supernatant failed to bind to $PLA_2$-Sepharose.

The present invention provides a technique to allow the development of GIF-producing T-cell populations from PBMC of patients allergic to bee venom $PLA_2$, and to establish GIF-producing hybridomas from the T-cells. Representative hybridomas express CD3 determinants and $TCR\alpha\beta$, indicating that they are T-cell hybridomas. Furthermore, the TcR complex on the hybridomas appears to be functional. Both parent T-cells (Carini, et al., *J. Immunol. Methods*, 127: 221, 1990) and the majority of the GIF-producing hybridomas (Tables III, IV) produced IgE-BF upon cross-linking of CD3. Cross-linking of $TcR\alpha\beta$ on CL3 and AC5 clones by the monoclonal antibody WT31 and anti-MGG also resulted in the formation of IgE-BF (results not shown). Further testing of representative CD3[+] hybridomas showed that all of the CL3, BE12, AC5 and CS7 clones expressed both CD4 and CD8. Since BUC cells employed for construction of the hybridomas are CD4[−] CDB[−] (personal communication from Dr. J. Stobo), it is not clear whether the parent T-cells of the hybridomas co-expressed both CD4 and CD8.

The present experiments showed that some of the T-cell hybridomas produced antigen($PLA_2$)-binding GIF upon cross-linking of CD3 on the cells. This finding is in agreement with the fact that representative murine GIF-forming hybridomas formed antigen-binding GIF upon stimulation with antigen-pulsed syngeneic macrophages or by cross-linking of CD3 on the cells (Iwata & Ishizaka, *J. Immunol.*, 141: 3270, 1988, Iwata, et al., *J. Immunol.*, 145:3917, 1989), and suggested similarities between the antigen-binding GIFs from the two species. In the murine system, the antigen-binding GIF obtained from the hybridomas suppressed the in vivo antibody response in carrier (antigen)-specific manner. It was also found that the antigen-binding GIF from the hybridomas were composed of antigen-binding polypeptide chain and non-specific GIF (Jadieu and Ishizaka, in *Immune Regulation by Characterized Polypeptides*, G. Goldstein, et al., ed., Alan R. Liss, New York, p.595, 1987), and that the antigen-binding chain shared a common antigenic determinant 14-12 with those of the effector type suppressor T-cell factor (TseF) (Iwata, et al. ibid, 1989). Separate experiments have shown that both the monoclonal anti-lipomodulin antibody 141-B9 and anti-I-J antibodies bound not only GIF, but also non-antigen binding chain (I-J⁺ chain) of TseF and TsiF (Jardieu, et al., *J. Immunol.*, 188:1494, 1986, Steele, et al., *J. Immunol.*, 142: 2213, 1989). These findings collectively suggest that the antigen-binding GIF is identical to TseF. Parent T-cells of a representative murine Ts hybridoma 71B4 were obtained by stimulation of OVA-primed spleen cells by homologous antigen, followed by propagation of the antigen-activated T-cells in the presence of GIF. (Iwata & Ishizaka, *J. Immunol.*, 141: 3270, 1988). The same strategy was employed to obtain the parent cells of the human T-cell hybridomas in the present experiments. Indeed, both non-specific GIF and PLA₂-binding GIF from the human hybridomas bound to 141B9-Sepharose which previous studies had shown could also absorb murine TsFs (Steele, et al., *J. Immunol.*, 142: 2213, 1989). It could be that PLA₂ -binding GIF from the human T-cell hybridomas represents human antigen-specific TseF. However, it is still possible that the antigen-binding GIF may be a counterpart of murine TsiF. Recent experiments in our laboratory have shown that the typical murine helper T-cell clone D10. G4.1 can produce antigen-binding GIF, if the cells were procultured in the presence of a phospholipase A₂ inhibitor, and then stimulated with antigen(conalbumin)-pulsed antigen-presenting cells (Ohno, et al., *Internat. Immunol.*, 2: 257, 1990). It was also found that this antigen-binding GIF bound to the monoclonal antibody 14-30, which is specific for TsiF (Ferguson and Iverson, *J. Immunol.*, 136: 2896, 1986), rather than the monoclonal antibody 14-12. Green, et al., (*J. Mol. Cell Immunol.*, 3: 95, 1987) also reported that D10. G4.i clone produced antigen-binding TsF upon antigenic stimulation with UV-irradiated antigen-pulsed macrophages, and that this factor, together with accessory molecules, induced the generation of the effector type, antigen-specific Ts. Since PBMC from allergic patients contain helper T-cells, it is still possible that the antigen-binding GIF from the human hybridomas represents TsiF rather than TseF.

Takeuchi, et al., (*J. Immunol.*, 141: 3010, 1988) established Tse clones from PBMC of KLH-primed individuals, who had received repeated injections of a large dose of homologous antigen. Modulin, et al., (*Nature*, 322: 459, 1986) also established Ts clones from lesions of lepromatous leprosy patients. However, prior to the present invention, effector molecules mediating suppressor activity (TsF) from human Ts cells have not been identified. Similarities between human GIF and mouse GIF suggest that the PLA₂-binding GIF from human T-cell hybridomas may represent TsF from human suppressor T-cells. The T-cell hybridomas, which produce antigen-binding GIF, will facilitate biochemical characterization of the molecules. It has been repeatedly shown in the mouse that Ts as well as TsF (antigen-binding GIF) suppressed the in vivo IgE antibody response more effectively than the IgG antibody response (Ishizaka, et al., *J. Immunol.*, 114:110, 1975). If the allergen-binding GIF from the human T-cell hybridomas actually represent TsF, it is a reasonable expectation that the T-cell factor may suppress the ICE antibody response of the donor of parent T-cells.

EXAMPLE 4

PREPARATION Of HYBRIDOMA CELL LINES PRODUCING CEDAR POLLEN-SPECIFIC GIF

Japanese cedar pollen is a major allergen in Japan and causes seasonal allergic rhinitis and conjuctivitis in a large percentage of the population. In order to further test the general applicability of the teachings of the invention to other antigens, the methods for generating antigen-specific GIF-producing T-cells and T-cell hybridomas (described above) were applied to peripheral blood mononuclear cells from patients allergic to Japanese cedar allergen.

The major allergen in Japanese cedar (Sugi, *Cryptomeria japonica*) is a 40 kDa glycoprotein designated cryj-1 (Yasueda, et al., *J. Allergy and Clin. Immunol.*, 71:77, 1983). For these studies, the allergen was isolated from extracts of cedar pollen by this method with slight modifications. Briefly, pollen was defatted with ether, and extracted 3 times with 0.125M ammonium bicarbonate. Carbohydrate in the extracts were removed by hexadecyltrimethyl ammonium bromide. Protons in the extracts were precipitated with 80% saturated ammonium sulfate, and the precipitate dissolved in 0.05M Tris-HCl buffer, pH 7.8. After extensive dialysis against the Tris-HCl buffer, the protein fraction was applied to a DEAE cellulose column (DE-52, Whatman), and a flow-through fraction was obtained. The fraction was concentrated, dialyzed against 0.01M acetate buffer, pH 5.0, and applied to a CM cellulose column (CM-52, Whatman), which was equilibrated witch the buffer. The column was washed with the buffer, and proteins retained in the column eluted with 0.1M phosphate buffer containing 0.3M sodium chloride. Proteins in the eluate were further fractioned by gel filtration through a Sephacryl S-200 HR column to contain a major protein fraction containing cryj-1. The major protein in the fraction was 42 kDa as determined by SDS-polycrytamide gel electrophoresis, and N-terminal amino acid sequence of the protein was identical to that of cryj-1. The protein was conjugated to Affigel 10 at 1.5 mg/ml gel.

A synthetic phospholipase A₂ inhibitor, 2-(p-amylcinnamoyl)-amino-4-chlorobenzoic acid. (ONO-RS-082, ONO Pharmaceutical Co.) was used instead of recombinant human lipocortin I. Previous experiments had shown that ONO-RS-82 is a specific inhibitor of phospholipase A₂ and facilitates the generation of GIF-producing cells in mouse spleen cell cultures (Ohno, et at., *International Immunology*, 1:425, 1989). When spleen cells of ovabumin-primed mice were stimulated with ovalbumin, and antigen-activated T-cells were propagated with IL-2 in the presence of either 2 µM ONO-RS-082, or 3 µg/ml recombinant human lipocortin I, GIF-producing, antigen-specific T-cells were generated. Antigen stimulated T-cells and construction of T-cell hybridomas were carried out essentially the same as described above, except that purified cryj-1 was used as antigen, and ONO-RS-082 was employed as a phospholipase A₂ inhibitor. Thus, mononuclear cells were obtained from periheral blood of patients allergic to Japanese cedar pollen, and suspended in RPMI 1640 medium containing 10% fetal calf serum (FCS). A suspension of the mononuclear cells (3×10⁶ cells/ml) were cultured for 3 days in the presence of 10 µg/ml cryj-1. Non-adherent cells were recovered, resuspended in RPMI medium containing 10% FCS, (3×10⁵ cells/ml), and cultured for 4 days in the presence of 60 units/ml human IL-2 and 24 µM ONO-RS-082. Cells propagated in this manner were then recovered and fused with BUC cells to construct hybridomas.

Hybridomas were treated with the monoclonal anti-CD3 antibody SPB-T3b (Spits, et al., *Hybridoma* 2:423, 1983), and the presence of CD3 on the cells were tested by immunofluorescence. Only CD3+ hybridomas were subcloned by limiting dilution.

The CD3+ hybridoma clones were maintained in complete DME medium containing 10% FCS, and culture supernatant of each clone was assessed for the presence of GIF by using the 12H5 cells. Results obtained with hybridomas from one patient are shown in Table V. GIF activity was detected in culture supernatants of three hybridomas; 31E9, 31B7, and 32B4. Supernatants of the other two hybridomas, 31 H6 and 31 H3; appear to have weak GIF activity. Thus, the GIF-producing hybridomas were treated with anti-CD3 antibody followed by anti-mouse immunoglobulin, and the cells were cultured for 24 hr. Culture supernatants were then fractionated on cryj-1 coupled immunosorbent. The presence of GIF activity in the flow-through fraction and the acid-eluate fraction from the immunosorbent was assessed by using the 12H5 cells. The results included in Table V indicate that GIF from the 31 E9 cells bound to cryj-1-Affigel and could be recovered by elution at acid pH, whereas GIF from the 31B7 cells failed to bind to the antigen-coupled immunosorbent. The results indicate that the 31 E9 cells produce GIF having affinity for cryj-1, upon stimulation with anti-CD3.

TABLE V

PRODUCTION OF HUMAN CEDAR ALLERGEN-SPECIFIC HYBRIDOMAS[a]

| Hybridoma Clone | % rosette inhibition[b] (effluent/eluate) | GIF activity in cryj-1 Sepharose[c] unbound | GIF activity in cryj-1 Sepharose[c] bound |
|---|---|---|---|
| none | 0/23 | 0/29 | — |
| 31H6 | 20/13 (±) | 5/20 (−) | 12/10 (±) |
| 31A11 | 0/25 (−) | ND | — |
| 31E9 | 28/5 (+) | 0/22 (−) | 20/0 (+) |
| 31H3 | 23/12 (±) | 0/34 (−) | 38/16 (±) |
| 31B7 | 32/5 (+) | 20/5 (+) | 4/24 (−) |
| 31F7 | 0/26 (−) | ND | — |
| 32B4 | 22/0 (+) | 22/14 (±) | 38/22 (±) |

[a]Hybridomas in this table were derived from two separate experiments.
[b]Culture supernatants of unstimulated hybridomas were screened for the presence of GIF. Aliquots of 12H5 cells were incubated with culture supernatant of each hybridoma in the presence of mouse IgE. Culture supernatants of the 12H5 cells were filtered through CF50A to remove IgE, and filtrates were fractionated on lentil lectin Sepharose. IgE-BF in the effluent and eluate fractions was assessed by rosette inhibition. Numbers in the column represent the percent rosette inhibition by the effluent eluate fractions from lentil lectin Sepharose. (+) (−) signs indicate the presence or absence of GIF, respectively.
[c]Representative hybridomas were treated with anti-CD3 antibody and culture supernatants were fractionated on cryj-1 coupled Affigel. The presence of GIF activity in the flow-through (unbound) fraction, and acid eluate (bound) fraction was determined by using 12H5 cells. Culture filtrates of the 12H5 cells were fractionated on lentil lectin Sepharose. Numbers represent percent rosette inhibition by the effluent/eluate fractions from lentil lectin Sepharose. GIF from the 31E9 cells bound to cryj-1-Affigel and was recovered by elution at acid pH, while GIF from the 31B7 cells failed to be retained in the cryj-1-Affigel column.

EXAMPLE 5

PREPARATION AND CHARACTERIZATION OF HYBRIDOMA CELL LINES PRODUCING MONOCLONAL ANTIBODIES SPECIFIC FOR HUMAN GIF

A. CONSTRUCTION AND SCREENING OF HYBRIDOMAS

Human GIF in culture supernatant of the T-cell hybridoma CL3 was purified by using anti-lipomodulin (141-B9)-Sepharose. The affinity-purified GIF was mixed in complete Freund's adjuvant, and BALB/c mice were immunized by intraperitoneal injections of the antigen, given 3 times at 2 week intervals. Two weeks after the last immunization, spleen cells of the immunized mice were obtained, and 1×10⁷ spleen cells were transferred into syngeneic BALB/c mice which had been irradiated with 625R γ ray. The recipients were immunized immediately after cell transfer and 2 weeks later with purified GIF included in incomplete Freund's adjuvant. One week after the booster, their spleen cells were fused with HPRT-deficient B cell line SP 2/0-14AG. The cells were cultured in HAT medium with BALB/c macrophages as feeder layer. One hundred and two hybridoma clones obtained in the culture were selected for the formation of mouse immunoglobulin, and Ig-forming hybridomas were selected for anti-GIF antibody production by ELISA assay, followed by bioassay using the 12H5 cells.

In ELISA assay, Immulon I plates (Dynatech) were coated with affinity-purified GIF. Control wells were filled with DPBS. After blocking the wells with 2% BSA, culture supernatants were applied to each well, and the binding of mouse Ig to the wells was determined by using alkaline-phosphatase-coupled anti-mouse Ig antibodies. As shown in Table VI, culture supernatants of 11 hybridoma clones gave a significant ELISA signal.

TABLE VI

Selection of Anti-GIF-Producing Hybridomas[a]

| Hybridoma Ig Clone | Isotype | ELISA Signal/Control[b] | GIF Activity[c] Effluent/Eluate |
|---|---|---|---|
| none | — | 0/0 | 29/1 (+) |
| 334F | IgM | 0.195/0.003 | 33/1 (+) |
| 355C | IgM | 0.388/0.012 | 28/0 (+) |
| 338H | IgM | 0.316/0.050 | 0/29 (−) |
| 318H | IgM | 0.149/0.046 | 0/31 (−) |
| 388F₁ | IgG₂ₐ | 0.892/0.100 | 0/28 (−) |
| 476B | IgM | 0.100/0.020 | 0/20 (−) |
| 489G | IgM | 0.174/0.00 | 7/15 (?) |
| 481F | IgM | 0.460/0.092 | 18/0 (+) |
| 335C | IgM | 0.203/0.073 | 0/27 (−) |
| 419A | IgM | 0.542/0.15 | 27/1 (+) |
| 312F | IgM | 0.533/0.029 | 14/8 (±) |
| Medium Control | — | 0/0 | 0/31 |

[a]Culture supernatants, which were positive in the ELISA assay, were assessed for the ability to bind GIF from CL3 clone.
[b]Binding of mouse Ig in culture supernatants of the hybridomas to GIF-coated wells, as compared with nonspecific binding of Ig in the same supernatants to BSA-coated wells. Optical density at 410 mµ.
[c]Mixtures of purified GIF with culture supernatants of hybridomas were filtered through YM100 membranes, and the filtrates were assessed for GIF activity. The 12H5 cells were cultured with mouse IgE in the presence of the filtrate. IgE-BF formed by the cells was fractionated on lentil lectin Sepharose and IgE-BF in the effluent and eluate fractions from the lectin-coupled Sepharose were assessed by rosette inhibition. Numbers represent the percent rosette inhibition by the effluent-eluate fractions. GIF switched the nature of IgE-BG formed by the cells (top column vs. bottom column). (+) indicates the presence of GIF.

The presence of anti-GIF in the culture supernatants of the 11 hybridoma clones was then determined by using the 12H5 cells (Iwata, et at., *J. Immunol.*, 140: 2534, 1988). The globulin factor of culture supernatant from each clone was obtained by precipitation with 50% saturated ammonium sulfate. After dialysis against phosphate buffered saline, the fraction was adjusted to ⅕ volume, of the original culture supernatant. Aliquots of an affinity-purified GIF prepared from CL3 clone using 141 B9 Sepharose. These aliquots were mixed with an equal volume of the globulin fraction from each clone, and the mixtures were incubated overnight at 4° C. The mixtures were then filtered through YM100 membranes, and the presence of GIF in the filtrates was assessed. Then, aliquots of a suspension of the 12H5 cells were mixed with an equal volume of the filtrate, and the cell suspensions were cultured for 24 hours in the presence of 10 µg/ml mouse IgE. The culture supernatants were filtered through CF50A membranes to remove IgE, and IgE binding factors in the filtrates were fractionated on lentil lectin Sepharose. The results of the experiments, included in Table VI, indicate that GIF was removed by the culture supernatants of 338H, 318H, 388F₁, 476B, and 335C clones, indicating that these hybridomas produce anti-GIF.

B. PURIFICATION OF HUMAN GIF WITH MONOCLONAL ANTI-GIF

Among the six hybridoma clones which produced monoclonal antibodies to GIF, only 388F₁ produced IgG antibody. This hybridoma was subcloned and cultured in high glucose Dulbecco's medium supplemented with 5% FCS. Culture supernatants were concentrated by ultra filtration and IgG in the supernatants was recovered by using Protein A-Sepharose. The monoclonal antibody was then coupled to Tresyl-activated Sepharose to prepare immunosorbent. In order to determine whether the monoclonal antibody could bind the same molecules as those bound to anti-lipomodulin (141B9) Sepharose, GIF in culture supernatant was absorbed with 141-B9-Sepharose, and was recovered by elution at acid pH. The affinity-purified GIF preparation was then fractionated with anti-GIF (388F₁)-coupled Sepharose. After the effluent fraction was obtained, the immunosorbent column was washed with 10 column volumes of Dulbecco's phosphate buffered saline (DPBS), and then eluted with glycine HCl buffer, pH 3.0. A serial dilution of the effluent and eluate fractions were assessed for GIF activity by using the 12H5 cells. The results shown in Table VII indicate that GIF in the acid eluate fraction from 141B9-Sepharose bound to the anti-GIF (388F₁)-Sepharose and was recovered again by elution at acid pH. The results indicate that both anti-lipomodulin and anti-GIF bind human GIF.

TABLE VII

Fractionation of Partially Purified Human GIF on the Anti-GIF (388F₁) Coupled Sepharose<sup>a</sup>

| Fraction from 388F₁-Sepharose | Dilution | GIF Activity<sup>b</sup> Effluent/Eluate |
|---|---|---|
| Effluent | 1:10 | 0/35 (−) |
|  | 1:20 | 0/29 (−) |
| Eluate | 1:20 | 39/0 (+) |
|  | 1:40 | 26/0 (+) |
| Unfractionated | 1:40 | 27/0 (+) |
| Media Control |  | 0/27 |

<sup>a</sup>GIF in culture supernatants of CL-3 clone was purified by using the anti-lipomodulin Sepharose. The affinity purified GIF (1.5 ml) was fractionated on 0.75 ml of 388F₁-coupled Sepharose. After recovering the effluent fraction, the column was washed with 10 column volumes of DPBS, and then eluted with 3 column volumes of glycine HCl, pH 3.0.
<sup>b</sup>GIF activity was assessed by using the 12H5 cells by the same procedures described in Table IV. Numbers in the column indicate the percentage rosette inhibition by the effluent/eluate fractions from lentil lectin Sepharose. (+) indicates the presence of GIF.

In order to determine if the anti-human GIF could bind mouse GIF, mouse GIF from Ts hybridoma, 231F₁ cells were purified by using 141B9-Sepharose, and aliquots of the purified mouse GIF were fractionated on either 141B9-Sepharose or 388F₁-Sepharose. After the effluent fractions were obtained, immunosorbents were washed with 3 column volumes of DPBS, and then eluted with 3 column volumes of glycine HCl buffer, pH 3.0. As expected, all GIF activity wag absorbed to 14189 Sepharose, and recovered by elution at acid pH. Neither the effluent nor washing fraction contained GIF activity. When the same GIF preparation was fractionated on 388F₁-Sepharose, weak GIF activity was detected in the effluent fraction. The majority of the activity was detected in washings with DPBS, but the acid eluate fraction did not contain a detectable GIF activity. It appears that mouse GIF bind to anti-human GIF with extremely low affinity, and disassociate from the immunosorbent by washing at neutral pH. These results indicate that the monoclonal antibody 388F₁ is specific for human GIF.

C. PURIFICATION OF HUMAN GIF BY ION EXCHANGE CHROMATOGRAPHY

AC5 cells were subcloned by limiting dilution and CD3⁻ clones obtained. These cells were then adjusted to serum-free ABC medium. Expression of CD3 on the subclones cultured in the medium was confirmed by fluorocytometry. Culture supernatants of CD3⁻ subclones were concentrated 10–30 fold, and GIF activity in serial dilutions of the preparations was determined. Based on these results, subclone (AC5-23) was selected, since a 1:3 dilution of the 10-fold concentrated supernatant of this subclone could switch the 12H5 cells from the formation of glycosylated IgE-BF to the formation of unglycosylated IgE-BF.

Studies were done to determine whether human GIF could be purified by ion-exchange column chromatography. Culture supernatant of the AC5 subclone in ABC medium was concentrated 25-fold. A 10ml aliquot of the concentrated culture supernatant was adjusted to pH 8.0 with Tris, diluted 8-fold with distilled water, and then applied to a DEAE-Sepharose column. Proteins bound to the column were eluted with 10 mM Tris buffers containing increasing concentrations of NaCl (see Example 1). Each fraction was concentrated to 10ml and assessed for GIF activity.

TABLE VIII

Distribution of GIF Activity in DEAE-Sepharose Fractions

| Fraction | Tris HCl + NaCl (mM)<sup>a</sup> | Protein Content (μg)<sup>b</sup> | GIF ACTIVITY<sup>c</sup> |
|---|---|---|---|
| 1 | 20 | 65.5 | 21/0 (+) |
| 2 | 50 | 35.0 | 20/6 (+) |
| 3 | 75 | 42.5 | 7/20 (−) |
| 4 | 100 | 38.5 | 3/19 (−) |
| 5 | 150 | 41.5 | 0/21 (−) |
| 6 | 200 | 42.0 | 0/20 (−) |
| medium control |  |  | 0/22 (−) |

<sup>a</sup>Concentrated culture supernatants of the AC5 cells were diluted 8-fold with distilled water, and applied to DEAE-Sepharose column. Fraction 1 represents passed through fraction combined with washing with 10 mM Tris HCl pH 8.0 containing 20 mM NaCl. The column was eluted stepwise with 10 mM Tris hCl containing increasing concentrations of NaCl.
<sup>b</sup>Total protein recovered after concentration of each fraction. After elution with Tris buffer containing 200 mM NaCl, much protein retained in the column.
<sup>c</sup>GIF activity was detected by using the 12H5 cells. Numbers represent the percent rosette inhibition by the affluent/eluate fractions from lentil lectin Sepharose. The proportion of RFC in the absence of IgE-BF was 22.6 ± 0.7 (SD) %. (+) (−) indicate the presence or absence of GIF.

As shown in Table VIII, the GIF activity was detected in the passed-through fraction and in the eluate with 50 mM NaCl, but not in the other fractions. Titration of a serial dilutions of the first two fractions indicated that the pass-through fraction had higher GIF activity than the 50 mM fraction.

Repeated experiments with a separate culture supernatant confirmed that the majority of GIF in culture supernatants could be recovered from a DEAE-Sepharose column, when culture supernatant of AC5 cells were concentrated 100-fold, diluted 3-fold with distilled water, and then passed-through the column. The passed-through fraction and washings with 10 mM Tris buffer containing 50 mM NaCl were combined, and concentrated to the original volume of the sample applied to DEAE-Sepharose. Titration of GIF activity in serial dilutions of the concentrated culture supernatant and the passed-through (50 mM NaCl) fraction showed that a 1:30 dilution of both samples could switch the 12H5 cells from the formation of glycosylated IgE-BF to the formation of unglycosylated IgE-BF. It was also found that 75 to 80% of protein in the culture supernatant could be removed by passing through the DEAE-Sepharose.

In order to estimate the molecular mass of GIF, 0.5 ml of the concentrated passed-through fraction from the DEAE-Sepharose was applied to a Superose-12 column and proteins were eluted at a flow rate of 1 ml/min. In this experiment, 5ml fractions were collected, and each fraction was assessed for GIF activity by using the 12H5 cells. GIF activity was detected in fraction 9, which was recovered between 70 and 75 min. Since Fractions 6 and 8 may also have a weak activity, GIF activity in the serial dilutions of fractions 6, 8, 9 was assessed. The GIF was detected in a 1:10 dilution of fraction 9, but not in a 1:2 dilution of the other fractions. The results suggested that the molecular mass of the major species of human GIF is in the range of 11 KDa to 18KDa. For better estimation of the size of GIF molecules, gel filtration on a Superose-I 2 was repeated in the same design, except that 1 ml fraction or 2.5 ml fractions were collected. Three separate experiments indicated that the majority of GIF was recovered between 68 and 72 min. It appears that the molecular mass of GIF is 12–18 KDa, as estimated by gel filtration.

Studies were also done identifying GIF by SDS PAGE. Two liter culture supernatant of the hybridoma in ABC medium were concentrated 100-fold, and fractionated on a DEAE-Sepharose column. Based on the experiments described above, the concentrated supernatant was diluted 3-fold with deionized water and passed through the DEAE-Sepharose. The passed-through fraction was concentrated, pre-absorbed with human IgG-coupled Sepharose, and GIF in the fraction was purified by affinity chromatography on the 388F1-coupled Affigel (see Example 1 ). In some experiments, the acid eluate fraction from the immunosorbent was adjusted to pH 8.0, and affinity-purification with 388F1-Affigel was repeated. Analysis of the affinity purified GIF preparation by SDS PAGE was performed under reduced and non-reduced conditions. The major band in the affinity-purified material has the molecular mass of 14KDa under reduced conditions and 15KDa under non-reduced conditions. In addition, a 67 KDa band was frequently observed. A portion of the affinity-purified preparation was dialyzed against DPBS and the GIF activity in the preparation was titrated. Assuming 100% recovery of GIF during dialysis and lyophilization, the sample applied to SDS-PAGE should have a GIF titer of 1:250.

Experiments were carried out to determine the relationship between the 14 KDa protein and GIF. The GIF in 2 liter culture supernatant of AC5 clone was purified by DEAE-Sepharose chromatography followed by affinity-purification using 388F1-Affigel. Acid eluates from the immunosorbent was adjusted to pH 8.0, concentrated to 1 ml by ultrafiltration and fractionated on a Superose 12 column. Every 2.5ml eluate fractions were assessed for activity by using the 12H5 cells. In this experiment, the majority of GIF activity was detected in the fraction eluated between 67.5 and 70 minutes. The presence of GIF in the fraction was confirmed by ELISA using biotin-coupled mAb 1 41-B9. Although the ELISA signal was weak, only the GIF-containing fraction gave ELISA signal. One ml of the GIF-containing fraction was lyophilized and analyzed by SDS PAGE. The results confirmed that the 14KDa peptide is present in the GIF-containing fraction.

Deposit of Materials

The following cell lines have been deposited with the American Type Culture Collection, 1301 Parklawn Drive, Rockville, Md., USA (ATCC):

| Cell Line | ATCC Accession No. | Deposit Date |
|---|---|---|
| 388F₁ | HB 10472 | May 31, 1990 |
| AC5 | HB 10473 | May 31, 1990 |
| 31E9 | HB X (not available yet) | June 2, 1992 |

These deposits were made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of deposit. The organisms will be made available by ATCC under the terms of the Budapest Treaty which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto including 37 CFR §1.14 with particular reference to 886 OG 638).

The assignee of the present application has agreed that if the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cell lines deposited, since the deposited embodiment is intended as a single illustration of one aspect of the invention and any cell lines that are functionally equivalent are within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fail within the scope of the appended claims.

I claim:

1. Substantially pure antigen-specific human glycosylation inhibiting factor (GIF), wherein the antigen is an allergen.

2. The antigen-specific GIF of claim 1, wherein the allergen is a venom component.

3. The antigen-specific GIF of claim 2, wherein the venom component is a honey bee venom component.

4. The antigen-specific GIF of claim 3, wherein the honey bee venom allergen is PLA₂.

5. The antigen-specific GIF of claim 4 which has the antigen binding specificity of the antigen-specific human GIF produced by cell line AC5 having ATCC accession number HB 10473.

6. The antigen-specific GIF of claim 4 which is produced by cell line AC5 having ATCC accession number HB 10473.

7. The antigen-specific GIF of claim 1, wherein the allergen is pollen.

8. The antigen-specific GIF of claim 7, wherein the pollen is tree pollen.

9. The antigen-specific GIF of claim 8, wherein the tree pollen is cedar pollen.

10. The antigen-specific GIF of claim 9 which has the antigen binding specificity of the human antigen-specific GIF produced by cell line 31E9 having ATCC accession number HB 11052.

11. The antigen-specific GIF of claim 9 which is produced by cell line 31E9 having ATCC accession number HB 11052.

12. A pharmaceutical composition comprising immunosuppressive amounts of substantially pitied antigen-specific human GIF and a pharmaceutically inert carrier, wherein the antigen is an allergen.

13. The pharmaceutical composition of claim 12, wherein the substantially purified antigen-specific human GIF has the antigen binding specificity of the antigen-specific human GIF produced by cell line AC5 having ATCC accession number HB 10473 or by cell line 31E9 having ATCC accession number HB 11052.

14. The pharmaceutical composition of claim 12, wherein the substantially purified antigen-specific human GIF is produced by cell line AC5 having ATCC accession number HB 10473 or by cell line 31E9 having ATCC accession number HB 11052.

* * * * *